United States Patent
Hirai

(10) Patent No.: US 10,386,304 B2
(45) Date of Patent: Aug. 20, 2019

(54) LIGHT MEASURING APPARATUS

(71) Applicant: HITACHI, LTD., Tokyo (JP)

(72) Inventor: Kakuro Hirai, Tokyo (JP)

(73) Assignee: Hitachi, Ltd., Tokyo (JP)

(*) Notice: Subject to any disclaimer, the term of this patent is extended or adjusted under 35 U.S.C. 154(b) by 0 days.

(21) Appl. No.: 16/163,600

(22) Filed: Oct. 18, 2018

(65) Prior Publication Data
US 2019/0154583 A1    May 23, 2019

(30) Foreign Application Priority Data

Nov. 17, 2017    (JP) ................... 2017-221410

(51) Int. Cl.
G01J 3/44       (2006.01)
G01N 21/65      (2006.01)
G01N 21/63      (2006.01)
G01N 21/64      (2006.01)

(52) U.S. Cl.
CPC .......... G01N 21/65 (2013.01); G01J 3/44 (2013.01); G01N 21/636 (2013.01); G01N 21/6458 (2013.01)

(58) Field of Classification Search
CPC ...... G01J 3/02; G01J 3/44; G01J 3/30; G01N 21/64; G01N 21/65; G01N 21/63; G01N 21/00; A61B 5/00; A61B 1/00; A61B 1/06; A61B 1/015; A61K 49/00; A61K 49/18; A61M 11/00
See application file for complete search history.

(56) References Cited

U.S. PATENT DOCUMENTS

2006/0238745 A1    10/2006  Hashimoto et al.
2013/0137944 A1*    5/2013  Jeong ............... A61B 1/015
                                                600/317

OTHER PUBLICATIONS

Cheng-Hao Chien, et al., "Label-free imaging of *Drosophila* in vivo by coherent anti-Stokes Raman scattering and two-photon excitation autofluorescence microscopy", Journal of Biomedical Optics, Jan. 18, 2011, vol. 16, No. 1.

Hideaki Kano, et al., "In-vivo multi-nonlinear optical imaging of a living cell using a supercontinuum light source generated from a photonic crystal fiber", Optical Society of America 2798, Apr. 3, 2006, vol. 14, No. 7.

* cited by examiner

*Primary Examiner* — Abdullahi Nur
(74) *Attorney, Agent, or Firm* — Mattingly & Malur, PC

(57) ABSTRACT

The invention is directed to a light measuring apparatus which is configured to generate broadband light from a laser beam emitted from a light source, the broadband light having a broader band than that of the laser beam, to divide the broadband light into a long wavelength component and a short wavelength component, to perform CARS measurement using the long wavelength component, and to perform fluorescence observation using the short wavelength component.

13 Claims, 10 Drawing Sheets

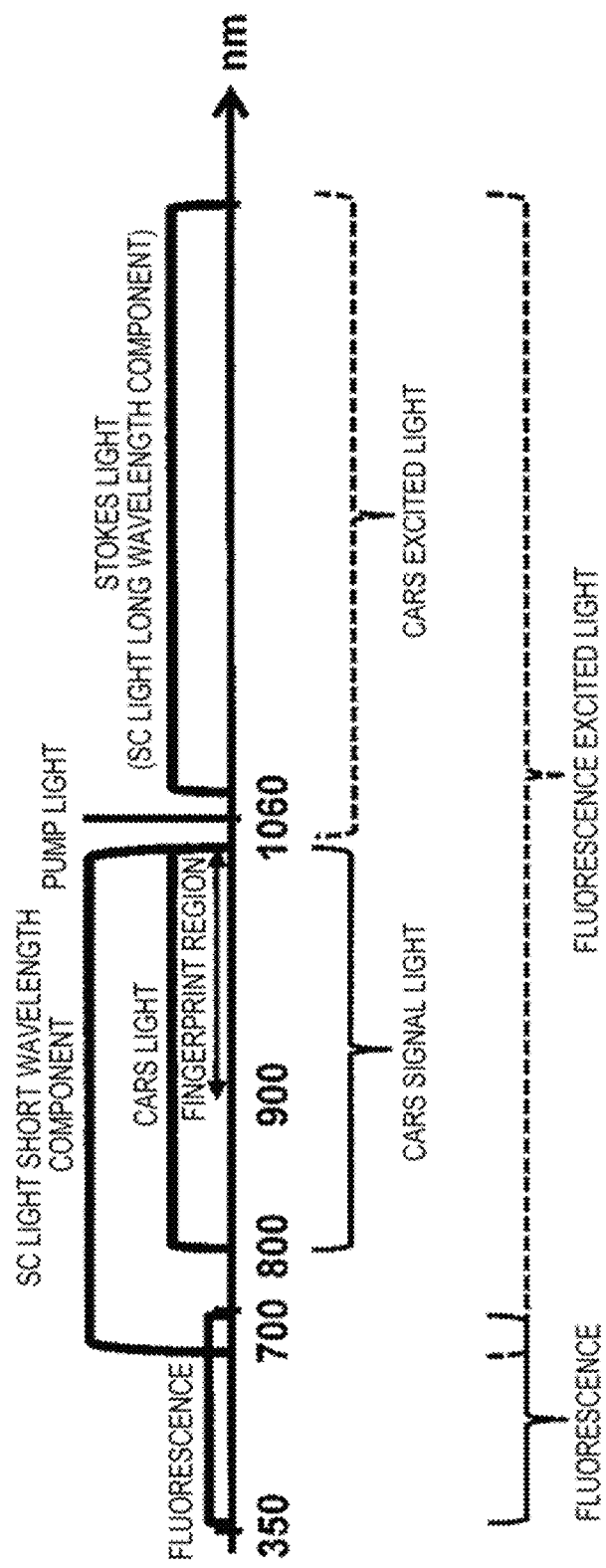

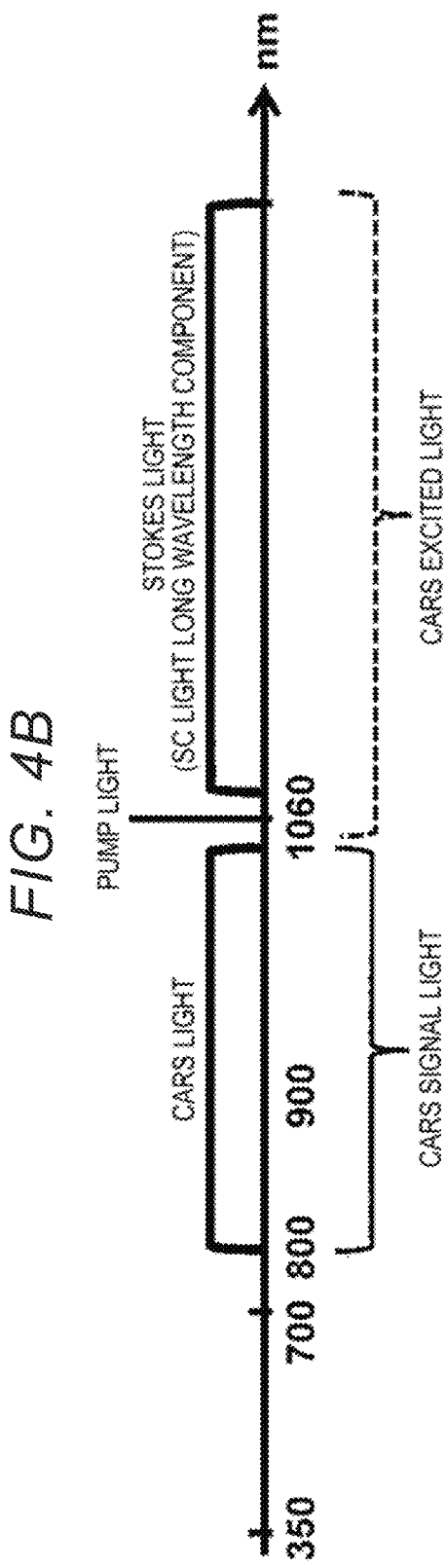

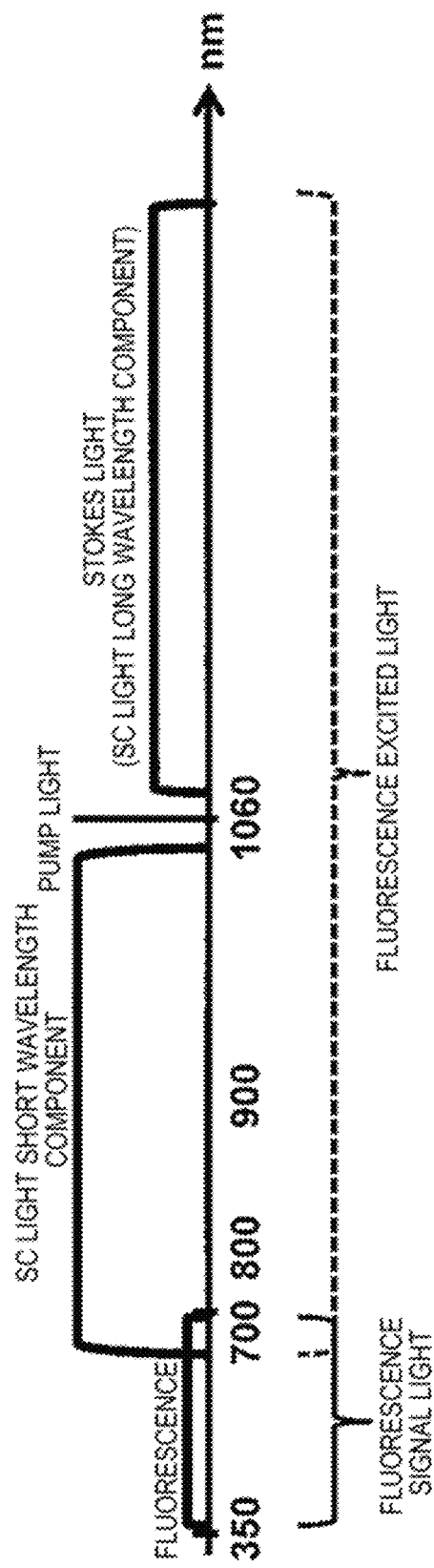

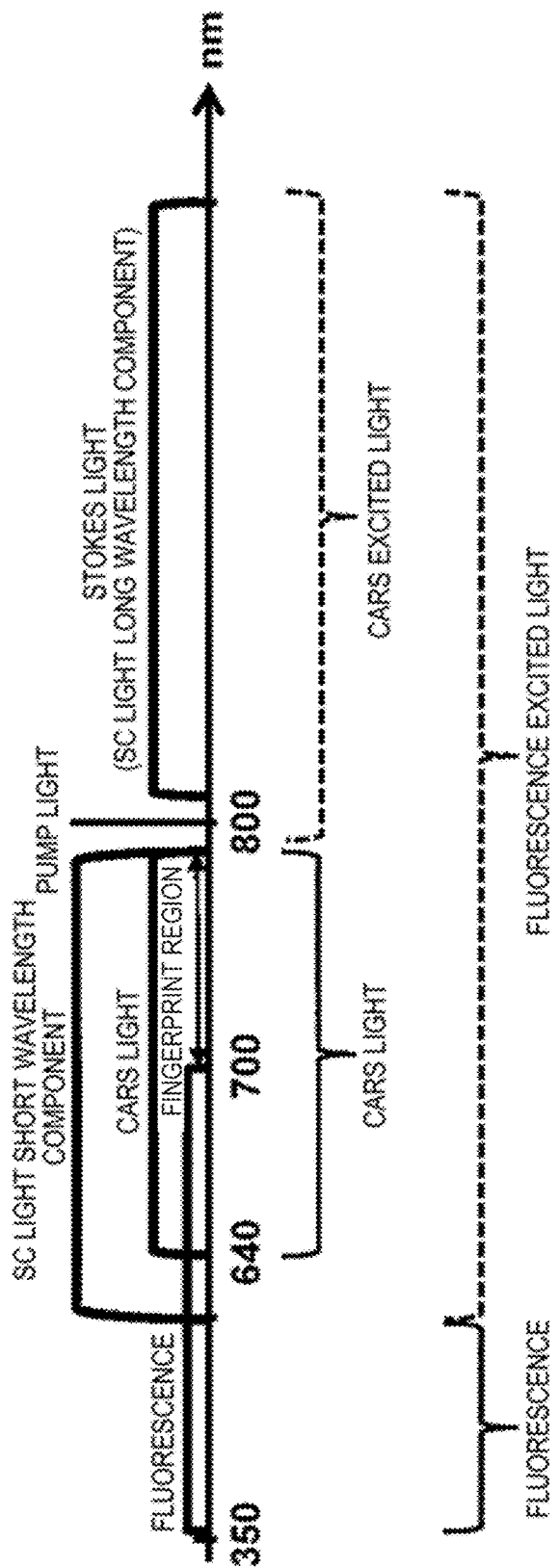

LIGHT MEASURING APPARATUS

BACKGROUND OF THE INVENTION

1. Field of the Invention

The present invention relates to a light measuring apparatus which measures a sample using light.

2. Description of the Related Art

In recent years, microscopes aiming at observing living tissues have been actively developed in medical and medicine development fields. Nowadays, a method of staining living tissue to be observed and observing it with a fluorescence microscope is common. However, it is difficult to continuously observe the same living tissue due to the influence of a staining reagent and thus a non-staining observation method has been demanded.

A Raman microscope is used to observe a Raman scattering light which implies a frequency shift of excitation light that derives out of scattering light generated by emitting an excitation laser beam to an object to be observed. The frequency shift represented by the Raman scattering light is referred to as a Raman shift, and a shifting amount depends on chemical bonding species distributed on a laser emission location. Thus, information regarding molecular species of the object to be observed and the distribution thereof may be obtained in a non-invasive and non-contact manner by obtaining Raman spectrums at a plurality of portions of the object by changing the laser emission location. Although the Raman microscope has the above-described features, the intensity of the Raman scattering light is low during ordinary Raman scattering called spontaneous Raman scattering and thus it takes time to perform measurement. Accordingly, the Raman microscope is difficult to be used for living tissue which significantly changes with time.

Recently, with the advent of high-performance short pulse laser, microscope technology using a nonlinear optical effect has been developed. In an existing fluorescence microscope, a sample is excited with a single photon using a light source corresponding to an excitation frequency co of each fluorescent material. A multiphoton excitation fluorescence microscope using the nonlinear optical effect excites a sample with multiple photons to satisfy $\omega=\Sigma(\omega i)$. Particularly, a multiphoton excitation fluorescence microscope which excites a sample with two photons is referred to as a two-photon microscope. The two-photon microscope has higher spatial resolution than a typical fluorescence microscope. Similarly, among Raman microscopes, a Coherent Anti-Stokes Raman Scattering (CARS) microscope, which uses the nonlinear optical effect to increase the intensity of a signal, has been developed. As a result, a measurement time can be reduced and living tissue can be observed using the Raman microscope.

CARS is a third-order nonlinear optical phenomenon using three types of laser such as pump light, Stokes light, and probe light, as excitation light. Generally, the probe light is replaced with the pump light to reduce the number of light sources. In this case, the intensity of CARS light is expressed by the following equation. $\chi^{(3)}$ represents a third-order electric susceptibility, $E_P$ represents an electric field of the pump light or the probe light, and $E_S$ represents an electric field of the Stokes light. The asterisk attached to the upper right of $E_S$ represents a complex conjugate.

$$I_{AS}(\omega_{AS}) \propto |\chi^{(3)} E_P^2(\omega_P) E^*_S(\omega_S)|^2$$

From the above description, the intensity of the CARS light is proportional to the intensity of the pump light to the second power and the intensity of the Stokes light to the first power. A molecule is coherently excited unlike in the spontaneous Raman scattering and thus the intensity of a signal of the CARS light is about $10^5$ times stronger than that of spontaneous Raman scattering light.

In recent years, for evaluation of living tissue, attempts have been made to increase the types of materials to be detected through integration of a CARS microscope and a fluorescence microscope (see, C. Chien, et al., "LABEL-FREE IMAGING OF *DROSOPHILA* IN VIVO BY COHERENT ANTI-STOKES RAMAN SCATTERING AND TWO-PHOTON EXCITATION AUTOFLUORESCENCE MICROSCOPY", JBO Vol. 16 No. 1 016012 (2011), and H. Kano, et al., "IN-VIVO MULTI-NONLINEAR OPTICAL IMAGING OF A LIVING CELL USING A SUPERCONTINUUM LIGHT SOURCE GENERATED FROM A PHOTONIC CRYSTAL FIBER", OSA Vol. 14 No. 7 2798 (2006)). Such a microscope is capable of specifically visualizing internal structures of the living tissue through fluorescence measurement and obtaining a distribution of molecular species in each of the internal structures through the CARS measurement. Alternatively, non-staining measurement which is a combination of measurement of autofluorescence of the living tissue and the CARS measurement may be performed. In US 2006/0238745 described below, an example of a device capable of performing both CARS observation and fluorescence observation is disclosed.

Since the technique disclosed in US 2006/0238745 uses a wavelength swept light source and thus equipment costs may be high or equipment size may be large.

SUMMARY OF THE INVENTION

To address the problem of the related art, the present invention is directed to providing a light measuring apparatus capable of performing CARS observation and fluorescence observation without using a wavelength swept light source.

In the light measuring apparatus according to the present invention, broadband light is generated from a laser beam emitted from a light source such that the broadband light has a band broader than that of the laser beam, and is divided into a long wavelength component and a short wavelength component, CARS measurement is performed using the long wavelength component, and fluorescence observation is performed using the short wavelength component.

The light measuring apparatus of the present invention is capable of performing CARS observation and fluorescence observation without using a wavelength swept light source and thereby can be manufactured to be smaller in size and at lower costs. Additional aspects, configurations, and effects of the present invention will be apparent from a description of embodiments to be described below.

BRIEF DESCRIPTION OF THE DRAWINGS

FIG. 4A illustrates a wavelength of each light when a short pulse laser beam source having a central wavelength of about 1060 nm is used;

FIG. 4B illustrates a wavelength of each light when CARS measurement is performed;

FIG. 4C illustrates a wavelength of each light when fluorescence measurement is performed;

FIG. 5 illustrates a wavelength of each light when the short pulse laser beam source having a central wavelength of about 800 nm is used;

DETAILED DESCRIPTION OF THE INVENTION

First Embodiment

Figure 1:
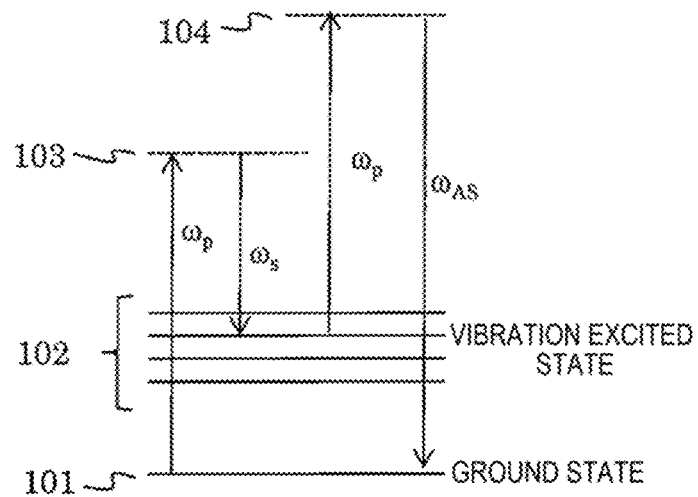
FIG. 1 is an energy level diagram illustrating a CARS process.

FIG. 1 is an energy level diagram illustrating a CARS process. A molecule which is in an initial state has a ground level 101. When pump light of a frequency $\omega_P$ and Stokes light of a frequency $\omega_S$ are simultaneously emitted to the molecule, the molecule is excited to an intermediate level 103 and then to a vibration excitation level 102. When probe light of a frequency cup is emitted to the molecule which is in an excited state, a sample emits CARS light of a frequency $\omega_{AS}$ in an intermediate level 104 and relaxes to the ground level 101. Accordingly, the CARS light is generated from the molecule having a vibration excitation level having a frequency of $\omega_P-\omega_S$. The frequency $\omega_{AS}$ is equal to $2\omega_P-\omega_S$.

Figure 2:
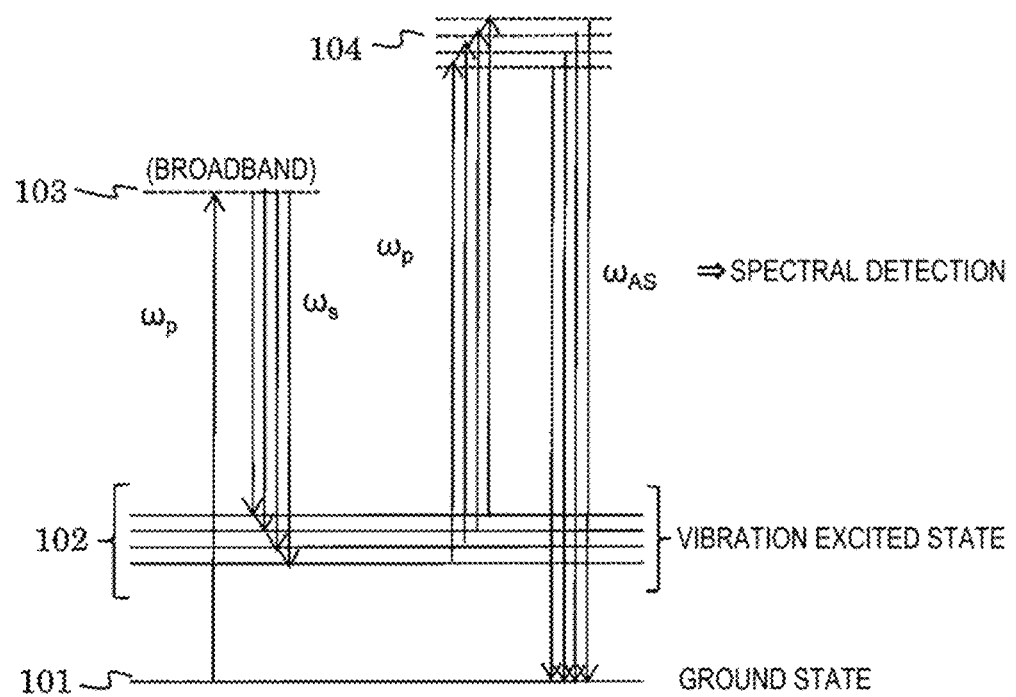
FIG. 2 is an energy level diagram illustrating a CARS process using broadband light.

FIG. 2 is an energy level diagram illustrating a CARS process using broadband light. In order to obtain a broadband spectrum in CARS measurement, a method of sweeping a wavelength of excitation light and a method of spectrally detecting CARS light generated using broadband light as Stokes light as illustrated in FIG. 2 may be used. The Stokes light is broadband and thus can be excited to the intermediate level 104 and then to a plurality of vibration excitation levels 102. CARS illustrated in FIG. 2 is referred to as multiplex CARS and spectral information may be obtained by performing exposure once.

Figure 3:
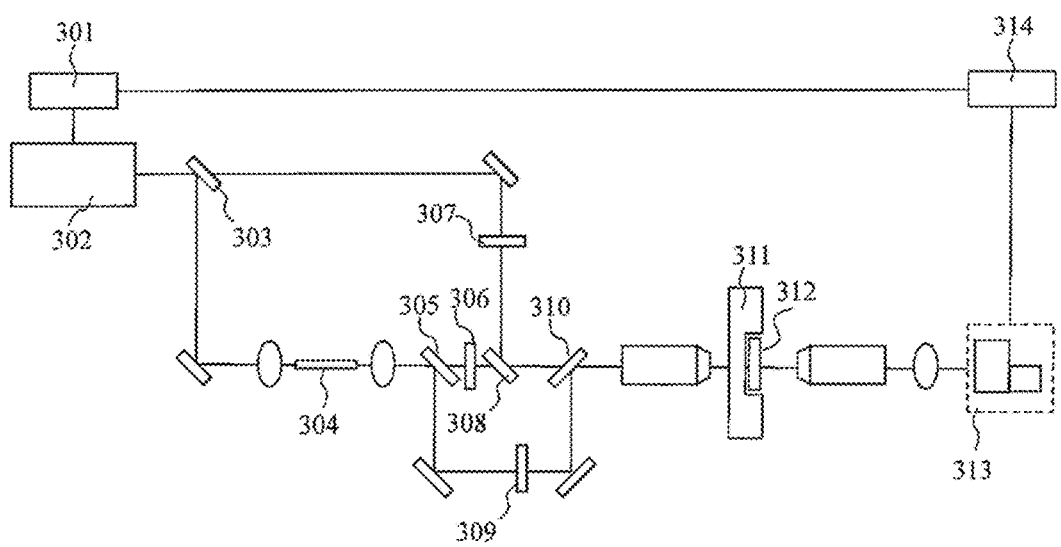
FIG. 3 illustrates an example of a configuration of a light measuring apparatus according to a first embodiment.

FIG. 3 illustrates an example of a configuration of a light measuring apparatus according to a first embodiment of the present invention. The light measuring apparatus according to the first embodiment includes a controller 301, an optical system (a short pulse laser beam source 302 to a detector 313), and an analyzer 314. The controller 301 controls overall operations of the light measuring apparatus. The optical system will be described hereinafter. The analyzer 314 obtains a hyperspectral image of an object 312 to be observed and performs a spectrum analysis on the hyperspectral image. The controller 301 and the analyzer 314 may be configured as a single device.

Light emitted from the short pulse laser beam source 302 is split into two parts by a beam splitter 303. One of the two parts split from the light is streamed into an optical fiber such as a photonic crystal fiber 304, and supercontinuum (hereinafter referred to as 'SC') light is generated in the optical fiber. A wavelength filter 305 extracts only a wavelength component which is longer than a wavelength of the light emitted from the short pulse laser beam source 302 and which is suitable for desired CARS measurement among the generated SC light. In the CARS measurement, the long wavelength component is used as Stokes light. The other part split from the light which is not used for generation of the SC light is used as pump light (as well as probe light) in the CARS measurement.

The terms "pump light" and "Stokes light" are used only when the CARS measurement is performed, but in order to further shed light on the present invention, each light is referred to as follows in the following description. (a) Light emitted from the short pulse laser beam source 302: pump light, (b) a long wavelength component used for the CARS measurement among the SC light: Stokes light or an SC light long wavelength component, and (c) a short wavelength component which is not used for the CARS measurement among the SC light: SC light short wavelength component.

A dichroic mirror 308 multiplexes the pump light and the Stokes light. Multiplex light obtained by multiplexing the pump light and the Stokes light is concentrated and emitted onto the object 312 to be observed, and thereby CARS light is generated. A dichroic mirror 310 multiplexes the SC light short wavelength component removed by the wavelength filter 305 with the pump light and the Stokes light. Multiplex light obtained by multiplexing the SC light short wavelength component with the pump light and the Stokes light is concentrated and emitted onto the object 312 to be observed, and thereby fluorescence is generated. The detector 313 may obtain a spectrum by detecting the CARS light and the fluorescence. An automatic stage 311 finely adjusts a focal point on the object 312 to be observed.

FIG. 4A illustrates a wavelength of each light when the short pulse laser beam source 302 having a center wavelength of about 1060 nm is used. In the CARS measurement, the object 312 to be observed is excited using a long wavelength component of SC light. A wavelength of CARS light (CARS signal light) generated accordingly overlaps the SC light short wavelength component.

FIG. 4B illustrates a wavelength of each light when the CARS measurement is performed. When the CARS measurement is performed, a wavelength filter 309 is inserted into an optical path of the SC light short wavelength component. As a result, the CARS signal light and the SC light short wavelength component may be prevented from overlapping each other, and the CARS measurement may be appropriately performed.

FIG. 4C illustrates a wavelength of each light when fluorescence measurement is performed. When the fluorescence measurement is performed, multiphoton excitation is performed using the SC light short wavelength component, the pump light, and the Stokes light. As a result, fluorescence (fluorescence signal light) is generated from the object 312 to be observed. In order to prevent damage to the object 312 to be observed, wavelength bands that are unnecessary for the measurement may be removed by inserting wavelength filters 306, 307, and 309 into an optical path of each light.

FIG. 5 illustrates a wavelength of each light when the short pulse laser beam source 302 having a center wavelength of about 800 nm is used. In the CARS measurement, the SC light short wavelength component is removed using the wavelength filter 309, similar to FIG. 4B. In the fluorescence measurement, the SC light short wavelength component partially overlaps a wavelength band of fluorescence excitation light, and thus, fluorescence caused by single photon excitation may be observed when an excitation wavelength of a fluorescent reagent to be used is included in a wavelength of the SC light short wavelength component.

When the single photon excitation is used, a wavelength of the fluorescent signal light does not largely shift from the wavelength of the fluorescence excitation light and thus may partially overlap the wavelength of the fluorescence excitation light. In this case, the wavelength filter 309 may be configured to remove the SC light short wavelength component of which a wavelength band overlaps that of the fluorescence signal light. When multiphoton excitation fluorescence is observed similar to FIG. 4C, the wavelength of the fluorescence signal light largely shifts from that of the fluorescence excitation light and thus such a filter configuration is likely to be unnecessary.

Figure 6:
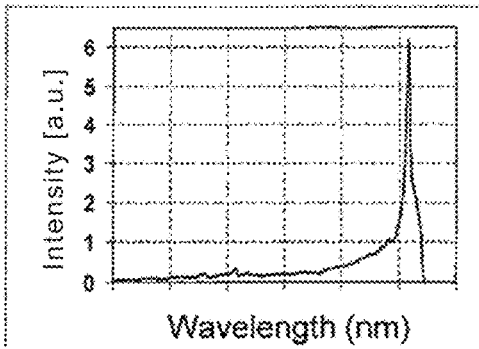
FIG. 6 illustrates an example of a screen of a user interface provided by a controller.

FIG. 6 illustrates an example of a screen for a user interface provided by the controller 301. The user interface includes a part for selecting a method of combining the CARS measurement and the fluorescence measurement or selecting a wavelength filter, as well as selecting a general measurement condition such as an exposure time. The user interface may include a part for displaying an obtained spectrum and a spatial intensity distribution of a specific wavelength. The controller 301 switches between performing one of the CARS measurement and the fluorescent measurement as instructed and performing both of them. Furthermore, the controller 301 switches which filter will be used or whether or not a filter will be used, as instructed.

Figure 7:
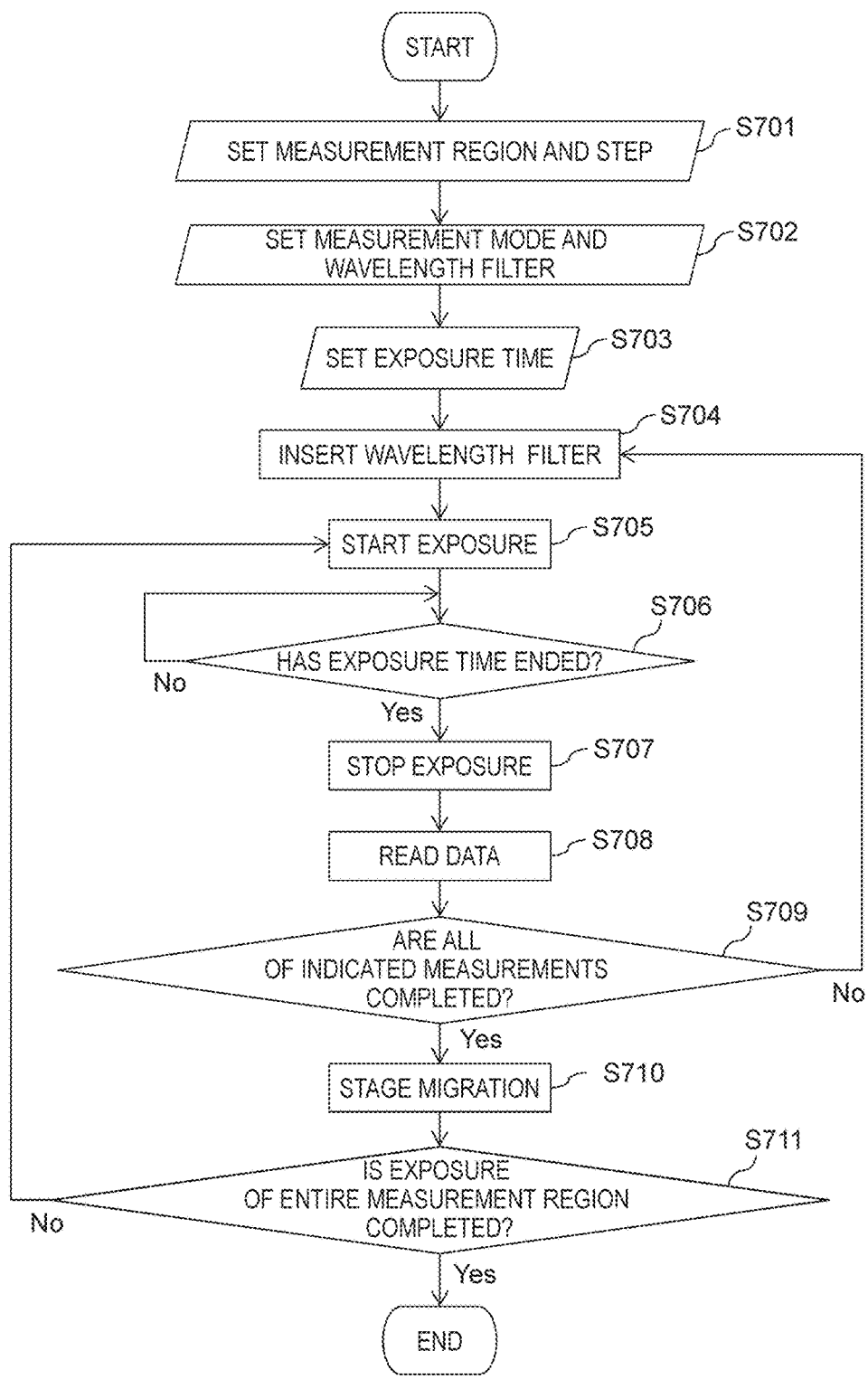
FIG. 7 illustrates a flowchart illustrating a method of performing measurement by the controller.

FIG. 7 is a flowchart demonstrating a measurement process performed by the controller 301. In S701, the controller 301 receives an instruction regarding a measurement region from a user via an interface. In S702, the controller 301 receives instructions regarding a measurement mode (whether or not measurement is to be performed) and a wavelength filter to be used with respect to each of the CARS measurement and the fluorescent measurement. The wavelength filter may be automatically selected by the controller 301 according to a wavelength band to be measured. The wavelength filter may not be selected when it is manually inserted or removed. In S703, the controller 301 receives an instruction regarding an exposure time. When performance of both the CARS measurement and the fluorescence measurement is instructed in S702, an exposure time of the CARS measurement and an exposure time of the fluorescent measurement are instructed. In S704, the controller 301 or the user inserts the instructed wavelength filter. In S705 to S708, the controller 301 measures one pixel. In S709, the controller 301 determines whether or not all the instructed measurements are completed. In S710, the controller 301 moves the object 312 to be observed to a next pixel position by using the automatic stage 311. In S711, the controller 301 determines whether or not the entire measurement region is measured.

First Embodiment: Summary

In a multiplex CARS microscope using broadband supercontinuum (SC) light as Stokes light according to the related art, a wavelength band which is longer than a wavelength $\lambda_P$ of pump light among the SC light is used as Stokes light and a short wavelength component which does not contribute to generation of CARS light is removed using a wavelength filter or the like. In the light measuring apparatus according to the first embodiment, the SC light short wavelength component is multiplexed with light corresponding to the pump light and the Stokes light and uses a result of the multiplexing as excitation light for the fluorescence observation. As a result, the CARS measurement and the fluorescence observation may be performed using a single device while including excitation wavelength bands necessary for general fluorescence observation. In addition, since the CARS measurement and the fluorescence measurement may be performed without using the wavelength swept light source, device size and costs may be reduced.

In FIG. 4C, the fluorescence measurement is performed using an entire wavelength region of the SC light short wavelength component. This is to make it possible to use the SC light short wavelength component in the entire wavelength range without limiting an excitation wavelength range of a fluorescent reagent. Accordingly, the wavelength filter 309 is used so that the CARS light and the SC light short wavelength component may not overlap each other. Alternatively, both the CARS measurement and the fluorescence measurement may be performed simultaneously when a fluorescent reagent that can be excited by the SC light short wavelength component of which a wavelength band does not overlap that of the CARS light is used. In the CARS measurement, when measurement is performed only on a fingerprint region which is supposed to contain a large amount of living tissue information of Raman, the fluorescence measurement may be performed together by using the SC light short wavelength component which does not overlap the fingerprint region.

Second Embodiment

Figure 8:
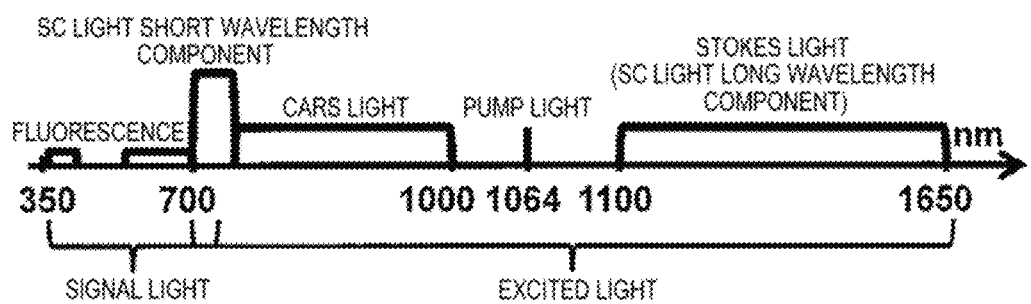
FIG. 8 illustrates a wavelength of each light used in a light measuring apparatus according to a second embodiment.

FIG. 8 illustrates a wavelength of each light used in a light measuring apparatus according to a second embodiment of the present invention. Since the SC light short wavelength component among the wavelengths described above with reference to FIG. 4A overlaps the CARS signal light, it is difficult to simultaneously perform the CARS measurement and the fluorescence measurement. Thus, in the second embodiment, a portion of the SC light short wavelength component a wavelength of which is being overlapped with that of the CARS signal light is removed using the wavelength filter 309. Accordingly, the CARS measurement and the fluorescence measurement may be performed at the same time. When the SC light short wavelength component is removed, a fluorescent component corresponding thereto decreases more than that of FIG. 4A, however, the configuration of the second embodiment is also useful as long as the decrease in the fluorescent component is allowed.

Third Embodiment

In the first embodiment, inserting or removing the wavelength filter 309 is inserted or removed to switch whether the SC light short wavelength component is to be emitted or not. In a third embodiment of the present invention, an example in which whether or not the SC light short wavelength component is to be emitted is switched in accordance with time decomposition using a high-speed shutter will be described below.

Figure 9:
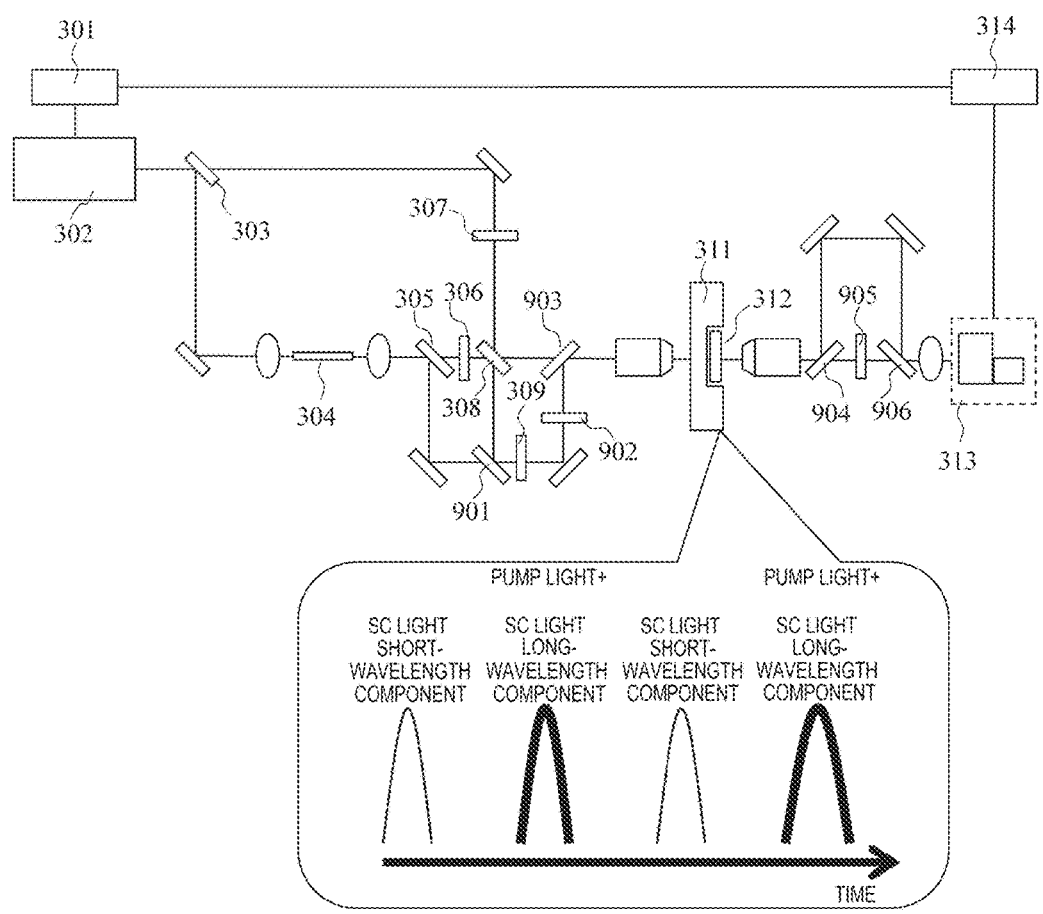
FIG. 9 illustrates an example of a configuration of a light measuring apparatus according to a third embodiment.

FIG. 9 illustrates an example of a configuration of a light measuring apparatus according to the third embodiment. A dichroic mirror 308 multiplexes pump light and Stokes light and then divides multiplex light into two parts. One of the two parts of the multiplex light is multiplexed with an SC light short wavelength component by a dichroic mirror 901. Multiplex light obtained by multiplexing the one part of the resultant light with the SC light short wavelength component is used as florescence excitation light, and the other part of the multiplex light is used as CARS excitation light. An optical path length adjustment mechanism 902 adjusts a timing of the fluorescence excitation light such that a timing at which the fluorescence excitation light is emitted onto the object 312 to be observed is different from a timing at which the CARS excitation light is emitted onto the object 312. A beam splitter 903 aligns the CARS excitation light and the fluorescence excitation light on the same optical axis.

When the fluorescence measurement is performed, a long-pass filter 904 is used to divide fluorescence on an optical axis. The long-pass filter 904 has an intermediate wavelength, as a cut-on wavelength, between a CARS light wavelength range and a fluorescence wavelength range. A long-pass filter 906 aligns the fluorescence, which is divided by the long-pass filter 904, again on the same optical axis. A high-speed shutter 905 blocks the fluorescence excitation light in synchronization with the timing adjusted by the optical path length adjustment mechanism 902. Thus, during the fluorescence measurement, the fluorescence excitation light is not incident on the detector 313. Accordingly, the detector 313 may detect the fluorescence.

The timings at which the CARS excitation light and the CARS signal light are incident on the detector 313 are different from the timings at which the fluorescence excitation light and the fluorescence are incident on the detector 313, and thus, they do not overlap on a time axis. Furthermore, the detector 313 may detect incident CARS signal light, since a wavelength of the CARS excitation light (the long wavelength component of the SC light) and a wavelength of the CARS signal light are different (that is, wavelength components thereof to be detected are different and the CARS excitation light and the CARS signal light can be individually detected: see FIGS. 4A to 5). A filter for removing the excitation light may be separately installed.

The high-speed shutter 905 may be optimally selected according to a repetition frequency of a light source. A mechanical chopper or the like may be used when a light source having a relatively low repetition frequency is used, and an optical switch or the like utilizing the Pockels effect or the Kerr effect may be used when a light source having a fast repetition frequency is used.

Third Embodiment: Summary

In the light measuring apparatus according to the third embodiment, the CARS light and the fluorescence are adjusted not to overlap each other on the time axis by the optical path length adjustment mechanism 902, and an SC light short wavelength component overlapping a wavelength of the CARS light is removed by the high-speed shutter 905. Thus, the CARS measurement and the fluorescence measurement may be carried out collectively. As a result, reducing detected noise or a detected time may be achieved, when compared to the first embodiment.

Fourth Embodiment

In the third embodiment, the CARS light and the SC light short wavelength component are temporarily separated from each other, so that the CARS measurement and the fluorescence measurement may be performed by performing measurement once. On the other hand, since it is necessary to arrange the optical path length adjustment mechanism 902 and the high-speed shutter 905, the device configuration is complicated. In a fourth embodiment of the present invention, the same effect as that of the third embodiment is achieved with a simpler and easier configuration than that of the third embodiment by adjusting the polarization of the excitation light.

Figure 10:
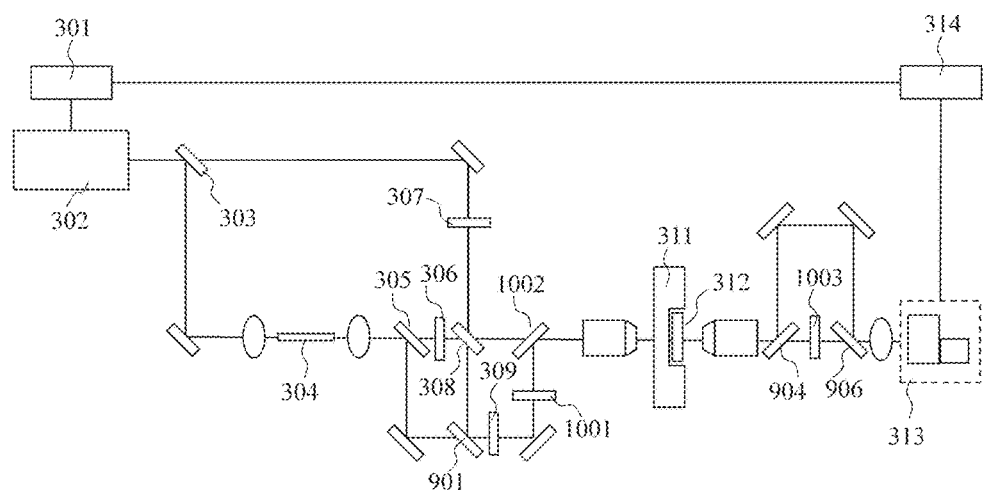
FIG. 10 illustrates an example of a configuration of a light measuring apparatus according to a fourth embodiment.

FIG. 10 illustrates an example of a configuration of a light measuring apparatus according to the fourth embodiment. An achromatic wavelength plate 1001 adjusts polarization of an SC light short wavelength component (fluorescence excitation light) to be different from polarization of an SC light long wavelength component (CARS excitation light). A polarization beam splitter 1002 multiplexes the fluorescence excitation light and the CARS excitation light. A polarization beam splitter 1003 removes a polarization component corresponding to the fluorescence excitation light. The other components of the light measuring apparatus according to the fourth embodiment are similar to those of the third embodiment. In the fourth embodiment, the CARS measurement and the fluorescence measurement are simultaneously performed by adjusting the polarization of excitation light and thus the same effect as in the third embodiment may be achieved with a simpler configuration.

Fifth Embodiment

Figure 11:
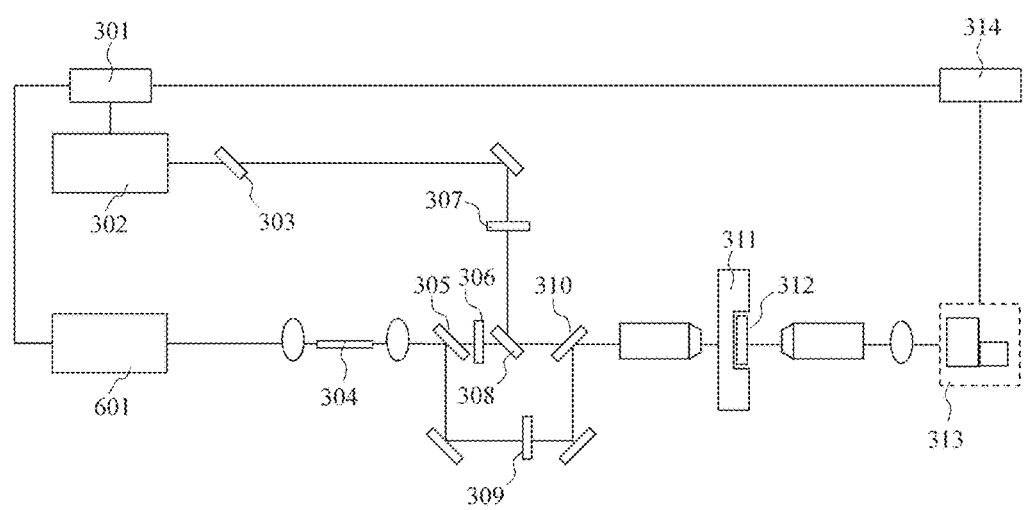
FIG. 11 illustrates an example of a configuration of a light measuring apparatus according to a fifth embodiment.

FIG. 11 illustrates an example of a configuration of a light measuring apparatus according to a fifth embodiment of the present invention. In the above embodiments, a laser beam emitted from the single short pulse laser beam source 302 is divided into the pump light and the excitation light by the beam splitter 303, but alternatively, two light sources may be provided such that the pump light is supplied from the short pulse laser beam source 302 and the excitation light is supplied from a short pulse laser beam source 601. In this case, a laser beam is supplied to a dichroic mirror 308 from the short pulse laser beam source 302, and a laser beam is supplied to a photonic crystal fiber 304 from the short pulse laser beam source 601.

Modified Examples

The present invention is not limited to the above-described embodiments but should be understood to include various modified examples. The above-described embodiments have been described in detail in order to explain the present invention in an easy-to-understand manner, and should not be limited to including all the configurations described herein. Furthermore, part of a configuration of one embodiment may be replaced with a configuration of another embodiment, and the configuration of the other embodiment may be added to that of the one embodiment. In addition, part of a configuration of each embodiment may be added to a configuration of another embodiment, be deleted therefrom, or be replaced therewith.

What is claimed is:

1. A light measuring apparatus for measuring a sample using light, comprising:
   a broadband light generator configured to generate broadband light by allowing a laser beam to pass therethrough, the broadband light having a broader band than a band of the laser beam;
   a wavelength divider configured to divide the broadband light into a long wavelength component having a wavelength longer than that of the laser beam and a short wavelength component having a wavelength shorter than that of the long wavelength component;
   a multiplexer configured to multiplex the laser beam and the long wavelength component to generate multiplex light;

a condensing optical system configured to concentrate the short wavelength component on the sample by concentrating the multiplex light on the sample;

a spectroscope configured to detect Raman scattering light generated by emitting the multiplex light to the sample; and a fluorescence detector configured to detect fluorescence generated by emitting the short wavelength component to the sample.

2. The light measuring apparatus according to claim 1, further comprising a filter configured to block at least a part of the short wavelength component, wherein the spectroscope detects the Raman scattering light when the filter blocks the short wavelength component, and the fluorescence detector detects the fluorescence when the filter does not block the short wavelength component.

3. The light measuring apparatus according to claim 2, wherein the filter blocks a portion of the short wavelength component overlapping a wavelength of the fluorescence.

4. The light measuring apparatus according to claim 1, further comprising a short-pass filter configured to block a part of the short wavelength component overlapping the Raman scattering light generated from the sample, wherein the spectroscope detects the Raman scattering light simultaneously with the detection of the fluorescence by the fluorescence detector, and the fluorescence detector detects the fluorescence simultaneously with the detection of the Raman scattering light by the spectroscope.

5. The light measuring apparatus according to claim 1, further comprising:

a timing adjuster configured to adjust a timing at which the short wavelength component is emitted to the sample to be different from a timing at which the multiplex light is emitted to the sample; and a blocking unit configured to block the short wavelength component in an optical path after the short wavelength component passes through the sample, in synchronization with the timing at which the short wavelength component is emitted to the sample, wherein the fluorescence detector detects the fluorescence while the blocking unit blocks the short wavelength component.

6. The light measuring apparatus according to claim 5, further comprising a long-pass filter configured to separate the fluorescence in the optical path after the short wavelength component passes through the sample, wherein the fluorescence detector detects the fluorescence separated by the long path filter.

7. The light measuring apparatus according to claim 1, further comprising:

a polarization adjuster configured to adjust polarization of the short wavelength component to be different from that of the multiplex light; and a divider configured to divide a polarization component of the short wavelength component after the short wavelength component passes through the sample, wherein the divider divides the polarization component of the short wavelength component not to be incident on the spectroscope.

8. The light measuring apparatus according to claim 7, further comprising a long-pass filter configured to separate the fluorescence after the short wavelength component passes through the sample, wherein the fluorescence detector detects the fluorescence separated by the long path filter.

9. The light measuring apparatus according to claim 1, further comprising:

a light source configured to emit the laser beam; and a divider configured to divide the laser beam into a component to be incident on the multiplexer and a component to be incident on the broadband light generator.

10. The light measuring apparatus according to claim 1, further comprising a first light source and a second light source configured to emit the laser beam, wherein the first light source emits the laser beam to the multiplexer, and the second light source emits the laser beam to the broadband light generator.

11. The light measuring apparatus according to claim 1, further comprising an interface configured to receive an instruction input instructing to switch whether to detect the Raman scattering light by the spectroscope or detect the fluorescence by the fluorescence detector, wherein the light measuring apparatus switches whether the Raman scattering light is to be detected by the spectroscope or the fluorescence is to be detected by the fluorescence detector on the basis of the instruction input received via the interface.

12. The light measuring apparatus according to claim 2, further comprising an interface configured to receive an instruction input instructing the filter to switch whether or not to block the short wavelength component, wherein the light measuring apparatus switches whether or not the short wavelength component is to be blocked by the filter on the basis of the instruction input received via the interface.

13. The light measuring apparatus according to claim 1, wherein the broadband light generator generates supercontinuum light as the broadband light.

* * * * *